United States Patent [19]

Balg et al.

[11] 4,117,000

[45] Sep. 26, 1978

[54] PROCESS FOR PREPARING 4-OXOCAPRONITRILE

[75] Inventors: Theodorus Balg, Brunssum; Constant M. A. Cramers, Obbicht; Hendrikus J. G. Maessen, Roermond, all of Netherlands

[73] Assignee: Stamicarbon, B.V., Geleen, Netherlands

[21] Appl. No.: 827,334

[22] Filed: Aug. 24, 1977

[30] Foreign Application Priority Data

Aug. 26, 1976 [NL] Netherlands .......................... 7609478

[51] Int. Cl.$^2$ .................... C07C 121/34; C07C 120/00
[52] U.S. Cl. ..................................... 260/465.1; 203/58; 203/62; 203/68; 203/69

[58] Field of Search ................ 260/465.1; 203/62, 69, 203/58, 68

[56] References Cited

U.S. PATENT DOCUMENTS

| 2,850,519 | 9/1958 | Krimm .......................... 260/465.1 X |
| 3,780,082 | 12/1973 | Deumens et al. ................. 260/465.1 |
| 3,816,503 | 6/1974 | Van Poelvoorde et al. ........ 260/464 |

Primary Examiner—Joseph Paul Brust
Attorney, Agent, or Firm—Cushman, Darby & Cushman

[57] ABSTRACT

A process is described for improving the synthesis of 4-oxocapronitrile by adding an inert solvent to the atmospheric pressure distillation of the reaction mixture so that the temperature of said distillation is maintained below about 195° C.

3 Claims, No Drawings

PROCESS FOR PREPARING 4-OXOCAPRONITRILE

This invention relates to an improved process for preparing 4-oxocapronitrile (5-oxohexanenitrile) by reacting acetone (in excess) with acrylonitrile by means of a primary amine and/or Schiff base as a catalyst in the presence of an acid compound. More particularly, this invention pertains to improvements in the recovery of the desired product from the reaction mixture, e.g.,

BACKGROUND OF THE INVENTION

The basic process of this type is already well-known. See, for instance, U.S. Pat. Nos. 3,780,082 and 3,816,503. These patents also addressed themselves to the problem of product recovery.

Thus, U.S. Pat. No. 3,780,082 discloses that after termination of the reaction, the reaction mixture is distilled at atmospheric pressure. The distillate thus obtained contains the catalyst and the unused reactants. This distillate is recycled, or re-used, for the preparation of additional amounts of 4-oxocapronitrile. The bottoms residue that remains from such distillation contains the desired 4-oxocapronitrile product. This residue is then distilled at a reduced pressure, and the desired oxo-nitrile product was then recovered as distillate in a virtually pure condition (see e.g., Example IV of U.S. Pat. No. 3,780,082).

The later U.S. Pat. No. 3,816,503 discloses that in this process a difficulty arose in that polymer formation occurred, in the reaction vessel, which impeded continuous operation of the process. This patent further taught that by maintaining the oxygen level in the reaction mixture below about 20 parts by weight per million, the deposition of the polymer-like substance into the wall of the reactor and onto the stirrer could be avoided, and the highest then possible yields could be maintained.

Now, however, further study of said process has shown that when temperatures of over 195° C are used in the atmospheric pressure distillation of the catalyst and the unconsumed reactants, the yield of 4-oxocapronitrile considerably decreased. It has been further observed, however, that when the said resulting reaction mixture is distilled in a column at atmospheric pressure, the bottom temperature of the column will in fact be considerably higher than 195° C. On the other hand, if this distillation was carried out at reduced pressure in order to maintain a bottom temperature below 195° C., and thus to prevent the decrease in yield, it was then found that recirculation of the distillate to the fresh reaction mixture then led again to the formation of a deposit of a rubber-like substance on the reactor wall and the stirrer — even though the content of dissolved oxygen in the fresh reactants was not changed and was kept below the level of 20 parts by weight per million to obtain a reaction mixture having also a content of dissolved oxygen below said level.

It can thus be appreciated that despite the advances made in the prior art teachings, practical difficulties in the continuous operation of this process and the recovery of product have still been present and have needed to be overcome.

OBJECT OF THE INVENTION

It is an object of this invention to provide an improved combination of process steps for the aforesaid process which improve the yield and continuity of the reaction and the recovery of the desired oxo-nitrile reaction product.

DESCRIPTION OF THE INVENTION

It has now been found according to this invention that in the atmospheric pressure distillation the temperature can be kept below 195° C., at a pressure not lower than atmospheric, by adding to the reaction mixture an inert solvent with a boiling point of between 80° and 195° C. When this is done, the recirculation of the resulting distillate does not cause the heretofore-observed deposits of the polymer-like substance.

Thus, according to the invention, the process for preparing 4-oxocapronitrile by reacting excess acetone with acrylonitrile in the presence of a primary amine and/or Schiff base as a catalyst and in the presence of an acidic compound, in which the amount of oxygen dissolved in the reaction mixture is kept below 20 parts by weight per million, and in which the unconsumed reactants and the catalyst are distilled off from the resulting reaction mixture and the 4-oxocapronitrile is recovered from the remaining residue, is now characterized by the improvement that the unconsumed reactants and the catalyst are first distilled off in the additional presence of an inert solvent having a boiling point of between 80° and 195° C., under a pressure not lower than atmospheric and whereby a temperature of below 195° C. can be maintained.

Examples of suitable inert solvents which may be employed are mesityl oxide, mesitylene, toluene, xylenes, decalin, dioxane, and cumene.

The minimum amount of such inert solvent to be added to the reaction mixture, when the unconsumed reactants and the catalyst are distilled off, is that amount at which the temperature of 195° C. is just not exceeded in distilling at atmospheric pressure. If more than said minimum amount of inert solvent is used, the maximum temperature during distillation can be reduced to, e.g., 180° C. Addition of such an amount of the inert solvent that said maximum temperature is reduced to below 160° C., is possible, but offers no additional advantage in practice.

After the unconsumed reactants and the catalyst have been distilled off, the inert solvent can be recovered from the remaining residue by distillation.

The preferred inert solvent to be used is mesityl oxide, since it is already formed as a by-product in the condensation of acetone to diacetone alcohol (followed by splitting of water) and has to be removed in any event during the distillation of the residue that remains after the first distillation of the unconsumed reactants and the catalyst and from which residue the 4-oxocapronitrile has yet to be recovered. Even though the mesityl oxide thus obtained in said distillation is contaminated, this presents no obstacle to its being used as the inert solvent in this process.

The distillation of the residue from which the inert solvent and the 4-oxocapronitrile are to be recovered can now be effected at reduced pressure without the problems previously encountered.

The low oxygen content required in the reaction mixture can be achieved in the known way, e.g., by passing an inert gas through the reaction mixture, and/or the reactants to be fed thereinto, or by distillation of the said reactants.

As taught in said prior patents mentioned above, the catalyst used in the process according to the invention may be any of various primary amines and/or Schiff bases, such as, e.g., methyl amine, ethyl amine, n-propyl amine, isopropyl amine, n-butyl amine, isobutyl amine, secondary pentyl amine, and/or the Schiff bases of these amines with acetone previously used. The amount of the catalyst may be varied. For practical purposes an amount of 0.01 to 0.25 mole of catalyst per mole of acrylonitrile to be converted is sufficient. A small amount of acid or an acidic compound must also be present in the reaction mixture in addition to the catalyst. Both organic and inorganic acids are suitable for this purpose, such as, e.g., acetic acid, benzoic acid, adipic acid, hydrochloric acid, phosphoric acid and sulfuric acid. The acetone in the process, according to the invention, may be present in varied excess amounts. Usually an excess of about 2 to 12 moles of acetone per mole of acrylonitrile is used. An excess of acetone of over about 12 moles, e.g., 15 moles of acetone per mole of acrylonitrile, may be used, but offers no advantage in practice.

The temperature at which the reaction of acetone with acrylonitrile is effected may also be varied, e.g., within a temperature of between about 75° and about 230° C. The pressure is not critical, but must be sufficiently high so that the reaction mixture is at least in the liquid phase.

The invention will now be further illustrated by reference to the following illustrative Example.

EXAMPLE

A stainless-steel reactor (capacity of 6 liters), and provided with a stirrer was fed per hour with acetone (454 grams), acrylonitrile (350 grams), and a mixture (61 grams) containing catalyst (composed of 23% by weight of isopropyl amine, 2.5% by weight of benzoic acid and 74.5% by weight of acetone) and 2317 grams of a recycling mixture obtained as described below (and composed of 0.1% by weight of isopropyl amine, 95.5% by weight of acetone, 2.7% by weight of acrylonitrile and 1.7% by weight of isopropylidene isopropyl amine). The reaction mixture was thereafter passed successively through two additional reactors of the same type.

The reaction mixture in these reactors was kept under a nitrogen pressure of about 20 atmospheres, while the temperature of the reaction mixture was kept at about 180° C., by heating the reactors. The oxygen content of the acetone used had been reduced from about 50 p.p.m. to about 1.5 p.p.m. by passing virtually oxygen-free nitrogen therethrough. In the reactors, the total oxygen content of the reaction mixture was about 2 p.p.m. After the reaction mixture had passed through the last reactor, it was cooled and allowed to expand to atmospheric pressure. 3182 grams of reaction mixture were thus obtained, per hour. The reaction mixture contained 19.6% by weight of 4-oxocapronitrile, 2.1% by weight of acrylonitrile, and 71.5% by weight of acetone.

The conversion based on the acrylonitrile amounted to 84%, and that based on the acetone amounted to 16%. The yield of 4-oxocapronitrile was 86% with respect to converted acrylonitrile and 75% with respect to converted acetone.

This resulting reaction mixture was subsequently fed to a distillation column, along with so much mesityl oxide (contaminated with 20% by weight of 3-isopropyl aminopropionitrile) as an inert solvent that the total amount of mesityl oxide in the resulting mixture was about 30% by weight of the amount of 4-oxocapronitrile.

The distillation column was an adiabatic sieve tray column with an internal diameter of 5 cm., built up of 25 sieve trays and provided with a reflux cooler, a reflux splitter, and a circulating evaporator.

The column was fed continuously with 3380 grams per hour of the said reaction/solvent mixture at the eleventh plate from the top. The top pressure was atmospheric. The bottom temperature fluctuated between 188° and 192° C.; the reflux ratio was 0.5. The distillate (2400 grams per hour) contained 0.1% by weight of isopropyl amine, 94.8% by weight of acetone, 2.7% by weight of acrylonitrile, 1.7% by weight of isopropylidene isopropyl amine and 0.8% by weight of water and was recycled back to the first reactor. To prevent accumulation of water in the reactors when the distillate is recycled, the reaction water formed by reaction of isopropyl amine and acetone to isopropylidene isopropyl amine and water was removed by means of molecular sieves.

The bottom product (980 grams per hour) from the distillation column consisted mainly of 18.9% by weight of mesityl oxide, 5.1% by weight of 3-isopropyl aminopropionitrile, 64.1% by weight of 4-oxocapronitrile and 10.6% by weight of residue.

This bottom product was fed to a second distillation column of the same type as the first and operated continuously, but here the product was fed in at the sixteenth plate from the top and the column was operated at reduced pressure (top pressure 150 mm of Hg; bottom temperature 190° C.). The reflux ratio was 1-2. The distillate (238 grams per hour) from this column contained 185 grams per hour of mesityl oxide and 47 grams per hour of 3-isopropyl aminopropionitrile. Part of this distillate (82% by weight) was recycled to the first distillation column for use therein as the inert solvent.

The bottom product, 742 grams per hour, consisted substantially of 4-oxocapronitrile (623 grams per hour) and residue (104 grams per hour).

This bottom product was fed to a third distillation column of the same type as the first. This column was operated continuously and fed at the 21st plate from the top, the reflux ratio being 3, the top pressure 20 mm of Hg, and the bottom temperature ranging between 215° and 220° C. The distillate thus obtained (620 grams per hour) was 4-oxocapronitrile of 98% purity. The bottom product (122 grams per hour) contained 13% by weight of 4-oxocapronitrile in addition to residue.

COMPARATIVE EXAMPLE A

The experiment described in the example was repeated, using the same reactant mixtures, but without the inert solvent being added to the reaction mixture to be distilled. The unconsumed reactants and catalyst were then distilled off at reduced pressure (top pressure 500 mm of Hg); in order to maintain a bottom temperature of 190° C.

After 10 hours a polymer-like substance had formed on the stirrer and the walls of the reactors. The oxygen content of the reaction mixture in the first reactor had in fact risen by the leak-in of air to 40 p.p.m.

COMPARATIVE EXAMPLE B

The experiment described in the example was again repeated, but again without an inert solvent being added to the reaction mixture to be distilled. The bottom temperature in the column, which was this time operated at atmospheric pressure to distil off unconsumed reactants and catalyst, amounted to 220°-225° C. In this case, the bottom product contained 30% by weight of residue, instead of only 10.6% by weight, as had been realized in the above example.

What is claimed is:

1. In a process for the preparation of 4-oxocapronitrile by reacting excess acetone with acrylonitrile by means of a primary amine and/or Schiff base as a catalyst and in the presence of an acidic compound, in which the amount of oxygen dissolved in the reaction mixture is kept below 20 parts by weight per million, and the unconsumed reactants and the catalyst are distilled off from the resulting reaction mixture and the 4-oxocapronitrile product is recovered from the remaining residue, the improvements consisting essentially in that the said distillation of unconsumed reactants and the catalyst is conducted at a pressure not less than atmospheric in the presence of a sufficient amount of an inert solvent having a boiling point of between about 80° and 195° C., such that a bottom temperature below about 195° C. is maintained.

2. The process of claim 1, wherein the distillate from said distillation is recycled to the said reaction.

3. In a process for the preparation of 4-oxocapronitrile by reacting excess acetone with acrylonitrile by means of a primary amine and/or Schiff base as a catalyst and in the presence of an acidic compound, in which the amount of oxygen dissolved in the reaction mixture is kept below 20 parts by weight per million, and the unconsumed reactants and the catalyst are distilled off from the resulting reaction mixture and the 4-oxocapronitrile product is recovered from the remaining residue, the improvements consisting essentially in that the said distillation of unconsumed reactants and the catalyst is conducted at a pressure not less than atmospheric in the presence of an added sufficient amount of mesityl oxide solvent such that a bottom temperature below about 195° C. is maintained throughout said distribution.

* * * * *